(12) United States Patent
Drobnitzky

(10) Patent No.: US 6,721,588 B2
(45) Date of Patent: Apr. 13, 2004

(54) MR SCANNER WITH A SETTING MECHANISM FOR PATIENT-DEPENDENT CONTROL OF THE RADIO-FREQUENCY FIELDS AND MAGNETIC FIELDS

(75) Inventor: Matthias Drobnitzky, Spardorf (DE)

(73) Assignee: Siemens Aktiengesellschaft, Münich (DE)

( * ) Notice: Subject to any disclaimer, the term of this patent is extended or adjusted under 35 U.S.C. 154(b) by 77 days.

(21) Appl. No.: 10/120,455

(22) Filed: Apr. 11, 2002

(65) Prior Publication Data

US 2002/0161294 A1 Oct. 31, 2002

(30) Foreign Application Priority Data

Apr. 26, 2001 (DE) .......................................... 101 20 578

(51) Int. Cl.⁷ .............................................. A61B 5/055
(52) U.S. Cl. ....................... 600/410; 600/413; 600/415; 324/322
(58) Field of Search ................................. 600/410, 411, 600/415, 413, 418; 324/318, 322; 378/206

(56) References Cited

U.S. PATENT DOCUMENTS 5,178,146 A * 1/1993 Giese ......................... 600/411
6,269,501 B1 * 8/2001 Li et al. ......................... 5/601
6,460,206 B1 * 10/2002 Blasche et al. ................. 5/601
6,614,536 B1 * 9/2003 Doemens et al. ........... 356/601
6,636,041 B2 * 10/2003 Arz et al. ................... 324/322
2002/0161294 A1 * 10/2002 Drobnitzky ................ 600/410
2002/0163337 A1 * 11/2002 Drobnitzky et al. ........ 324/318

FOREIGN PATENT DOCUMENTS

DE 199 19 925 11/2000

OTHER PUBLICATIONS

Patent Abstracts of Japan, Publication No. 03284241 Application No. 02087077.

* cited by examiner

Primary Examiner—Shawna J. Shaw
(74) Attorney, Agent, or Firm—Schiff Hardin LLP

(57) ABSTRACT

An MR scanner with a setting mechanism for patient-dependent control of the radio-frequency fields and magnetic fields for adhering to individual SAR and dB/dt limits, has an optical measuring device containing a distance sensor for determining the surface of a patient and for determining a setting signal for the setting mechanism.

7 Claims, 1 Drawing Sheet

MR SCANNER WITH A SETTING MECHANISM FOR PATIENT-DEPENDENT CONTROL OF THE RADIO-FREQUENCY FIELDS AND MAGNETIC FIELDS

BACKGROUND OF THE INVENTION

1. Field of the Invention

The present invention is directed to an MR scanner of the type having a setting mechanism for patient-dependent control of the radio-frequency fields and magnetic fields for adherence to individual SAR and dB/dt limits.

2. Description of the Prior Art

Modern high-performance MR tomography systems are to a high degree no longer hardware-limited with respect to the radio-frequency or gradient pulses that can be applied to the patient. On the contrary, SW and HW monitors must be utilized in order to assure that SAR and dB/dt limits are adhered to. This in turn limits many applications which have an optimum performance at the upper edge of the range of the characteristic quantities.

For example, the SAR calculation determines the maximum radio-frequency energy that can be applied on the basis of rough assumptions (model of a number of cylinders) based on the size of the patient under examination. The size of the patient is estimated in a table from the age and sex entered by the operator. A simplified body model likewise forms the basis in the calculation of the dB/dt stimulation. A source of error in common to both methods as conventionally implemented is that the individual body geometry of the patient deviates from the model formation. In any case, a conservative estimate, with a limitation of the application resulting therefrom, must be made.

The abstract of Japanese Application 03 284 241 discloses a method for determining a specific absorption rate (SAR). First, a rough magnetic resonance image of an examination subject is produced with a fast imaging method. A circle is drawn around the part of the examination subject of interest in the magnetic resonance image. The radius of the circle is determined. The radius of this circle is introduced into an equation for determining a number of excitations per time unit with an SAR value below a prescribable value. Finally, a series of excitation pulses is set with the number of excitations per time unit that has been thus identified as a limit.

SUMMARY OF THE INVENTION

An object of the present invention is to equip an MR scanner of the type initially described so that a patient-dependent control of the radio-frequency fields and magnetic fields can ensues in a simple way, and wherein limit values that are maximally but exactly adapted to the patient can be determined for an improved radio-frequency and gradient pulse performance.

This object is inventively achieved in an MR scanner having an optical measuring device containing a distance sensor preferably arranged before the admission opening of the scanner above the patient table for detecting (identifying) the surface of a patient and for defining a setting signal for the setting mechanism.

The surface of the current patient thus can be measured with the assistance of a linearly or planarly resolving optical distance sensor in conjunction with a pulsed laser light source. CMOS sensors with an integration time of 30–40 nsec and a topical resolution of approximately 0.5 cm that have recently because commercially available and do not contain any mechanical parts whatsoever and are completely integrated on a chip. An optical measuring device constructed therewith can be very easily integrated in MR scanners, and the laser that is already provided for use in positioning the patient can be advantageously simultaneously employed as a light-emitting device for the surface measurement.

Due to the enormously high speed of such sensors, the measurement of the surface of the patient can be implemented completely during the displacement time of the patient table, with the identified surface information of the current patient representing the exact input (size, dimensions, specific details of the body region) for the calculation of individually adapted SAR and dB/dt limits.

Particularly when a targeted acquisition of details of the body region of the patient to be examined additionally ensues corresponding to the scanner program that has been set, it is possible to avoid application limitations due to limit values that are pessimistic because they are only imprecisely known, and to instead carry out the examination with the RF and gradient performance that is maximally possible for the current patient.

DESCRIPTION OF THE PREFERRED EMBODIMENTS

Figure 1:
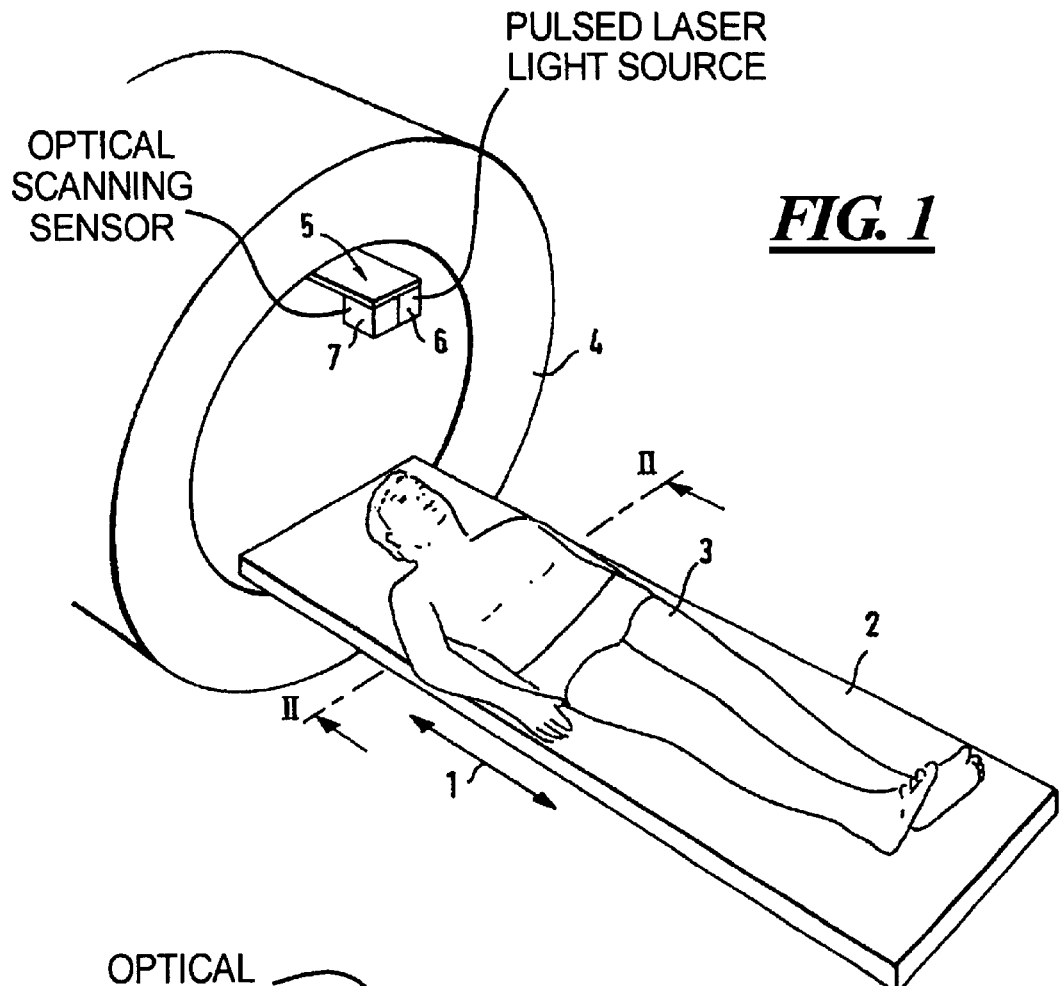
FIG. 1 is a perspective view of the admission region of an MR scanner with optical measuring device arranged above the patient table in accordance with the invention.
Figure 2:
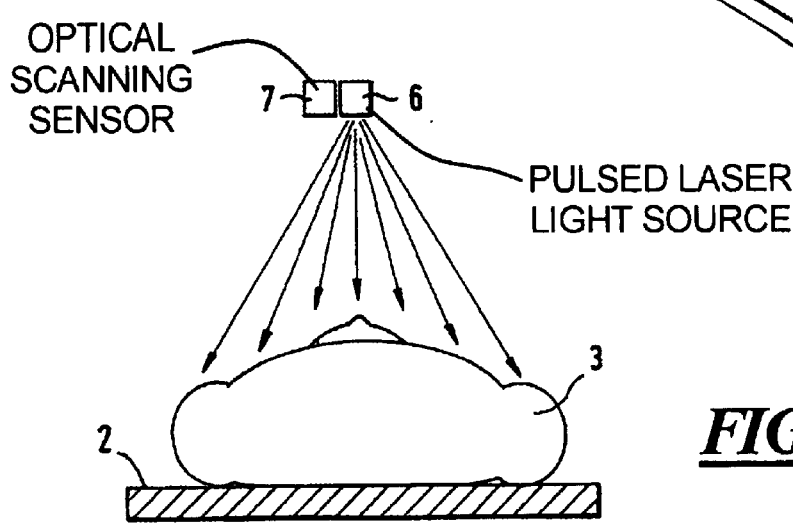
FIG. 2 is a cross-section along the line II—II in FIG. 1.

As shown in FIGS. 1 and 2, a patient 3 lying on a patient table 2, that is displaceable in the direction of the double arrow 1, is moved under an optical measuring device 5 when introduced into the MR scanner 4. The measuring device 5 has a pulsed laser light source and an optical scanning sensor 7. For the distance measurement, the laser 6 must illuminate the surface at least along one resolution direction of the scanning sensor 7, transversely relative to the longitudinal displacement direction 1 in the illustrated exemplary embodiment. The resolution in the second direction can be realized by the displacement of the patient table, so that there is no need for additional rotatability of the optical measuring device in this direction.

Although modifications and changes may be suggested by those skilled in the art, it is in the intention of the inventor to embody within the patent warranted hereon all changes and modifications as reasonably and properly come within the scope of his contribution to the art.

I claim as my invention:

1. In a magnetic resonance scanner having at least one radio-frequency coil which generates a radio-frequency field and at least one gradient coil which generates a gradient magnetic field, and a setting circuit for controlling said radio-frequency coil and said gradient coil to set said radio-frequency field and said gradient magnetic field within patient-dependent SAR and dB/dt limits, the improvement of said setting circuit comprising:

an optical measuring device having a field of view adapted to encompass at least a portion of a patient, for generating a signal representing an entirety of a surface of said patient facing said optical measuring device; and a unit supplied with said signal for determining a setting signal for said radio-frequency coil and said gradient coil dependent on said surface.

2. The improvement of claim 1 wherein said magnetic resonance scanner has an admission opening and a patient table adapted to receive a patient to move said patient through said admission opening, and wherein said optical measuring device is disposed at said admission opening above said patient table.

3. The improvement of claim 1 wherein said optical measuring device includes a pulsed laser light source adapted to direct a pulsed laser beam toward said patient, and an optical distance sensor disposed to detect said pulsed laser light source after interaction with said patient.

4. The improvement of claim 3 wherein said optical distance sensor is a linearly resolving optical distance sensor.

5. The improvement of claim 3 wherein said optical distance sensor is a planarly resolving optical distance sensor.

6. The improvement of claim 3 wherein said magnetic resonance scanner includes a control unit loaded with a scanner program for operating said radio-frequency coil and said gradient coil to conduct a scan, and wherein said improvement further comprises a routine in said program for controlling said optical measuring device to obtain a targeted acquisition of details of a body region of said patient dependent on said program.

7. The improvement of claim 6 wherein said laser light source simultaneously serves as a light aiming device for positioning a patient in said magnetic resonance scanner.

* * * * *